United States Patent
Spooner

(10) Patent No.: US 6,721,054 B1
(45) Date of Patent: Apr. 13, 2004

(54) METHOD AND APPARATUS FOR DETERMINING THE REFLECTANCE OF TRANSLUCENT OBJECTS

(76) Inventor: David L. Spooner, 2918 N. Franklin St., Wilmington, DE (US) 19802

( * ) Notice: Subject to any disclaimer, the term of this patent is extended or adjusted under 35 U.S.C. 154(b) by 0 days.

(21) Appl. No.: 09/958,450
(22) PCT Filed: Apr. 14, 2000
(86) PCT No.: PCT/US00/09900
§ 371 (c)(1),
(2), (4) Date: Oct. 11, 2001
(87) PCT Pub. No.: WO00/63676
PCT Pub. Date: Oct. 26, 2000

Related U.S. Application Data
(60) Provisional application No. 60/129,416, filed on Apr. 15, 1999.

(51) Int. Cl.[7] .............. G01N 21/55; G01N 1/10; H04N 1/46; G01J 5/02; G09G 5/02
(52) U.S. Cl. .............. 356/445; 356/243.1; 356/243.5; 356/308; 358/504; 358/509; 250/339.07; 345/600
(58) Field of Search .............. 356/243.1, 243.5, 356/243.8, 308, 319, 326, 328, 429, 445; 358/504, 509; 250/339.07, 559.01, 559.11; 345/600

(56) References Cited

U.S. PATENT DOCUMENTS 4,288,160 A * 9/1981 Lodzinski
5,028,139 A * 7/1991 Kramer et al.
5,047,652 A   9/1991 Lisnyansky et al. ........ 250/571
5,353,790 A * 10/1994 Jacques et al.
5,502,799 A   3/1996 Tsuji et al. .................. 395/131
5,790,281 A * 8/1998 Knox et al.
5,793,486 A   8/1998 Gordon et al. .............. 356/328

OTHER PUBLICATIONS

D. Spooner, "An automated measuring system incorporating an automatic correction for lateral diffusion error," SPIE Proc., vol. 3018 pp. 172–175 (1997).
D. Spooner, "A new method for determining lateral diffusion error in color measurements," SPIE Proc., vol. 2658 pp. 151–160 (1996).
D. Spooner, "Measurement without bounds," 1999 TAGA Proc., pp. 671–681 (May 5, 1999).
D. Spooner, "A spectral reflectometer which corrects for edge–loss error," SPE Color & Appearance Div., Sep. 18, 2000.
D. Spooner, "Effect of adjacent color on sample measured color," 2001 TAGA Proc., pp. 346–356 (2001).

* cited by examiner

Primary Examiner—Frank G. Font
Assistant Examiner—Khaled Brown
(74) Attorney, Agent, or Firm—RatnerPrestia

(57) ABSTRACT

A method for accurately measuring the reflectance of translucent objects by illuminating small areas of the object is disclosed. The method involves determining the lateral diffusion error by use of a predetermined set of calibration standards. The lateral diffusion error is added to the uncorrected reflectance to produce the corrected reflectance value. The method has widespread potential applications in the paper, printing, textile, coating, and food industries.

20 Claims, 5 Drawing Sheets

METHOD AND APPARATUS FOR DETERMINING THE REFLECTANCE OF TRANSLUCENT OBJECTS

This application claims that benefit of Provisional application Ser. No. 60/129,416, filed Apr. 15, 1999.

FIELD OF THE INVENTION

This invention relates to a method to determine the correct reflectance values of translucent objects at one or more spectral wavelengths and one or more illumination and viewing geometries. In particular, the method corrects for errors caused by lateral diffusion of instrument illumination light, within the object, to areas that cannot be viewed by the instrument detection system.

BACKGROUND OF THE INVENTION

The reflectance of an object is measured by illuminating some portion of the object with light from one or more directions and measuring the magnitude of the light reflected from the object in one or more directions. The light from the illuminating source may or may not passed through a monochromator or one or more spectral filters prior to illuminating the object. The light reflected by the object may or may not be passed through a monochromator or one or more filters prior to be evaluated by one or more detectors. If filters with one or more specific band passes are used and the instrument is calibrated with a reflectance standard, the instrument might be referred to as a filter reflectance densitometer or a filter calorimeter. If a monochromator is used and measurements are made at several wavelengths, the instrument would generally be referred to as a spectrometer. If the output of the spectrometer is referenced to a previously or concurrently measured calibration standard, the instrument is usually called a spectrophotometer. If a number of spectral reflectance measurements at specified wavelengths are made with the spectrophotometer and are processed a manner set forth by the CIE or ASTM ("Standard Practice for Obtaining Spectrophotometric Data for Object-Color Evaluation," ASTM Designation E 1164(83), American Society for Testing Materials, Philadelphia, Pa., incorporated herein by reference), the instrument and processor represents a spectrocolorimeter.

When the reflectance of a translucent object or material is measured, some of illuminating light laterally diffuses within the body of illuminated object to locations beyond the edge of the illuminating area. The laterally diffused light forms a dim halo around the illuminated area, and the intensity of the light near the edge of the illuminated area is reduced relative to that in the center of the area. If a detector views only the illuminated area, the measured reflectance value will be in error because the detector has not viewed the laterally diffused light.

Hsia, NBS Technical Note 594–12 (1976), has referred to this measurement error as translucent blurring error. Atkins and Billmeyer, Materials Res. and Std., 6 (1966), pp 564–569, refer to it as edge-loss error. Hunter and Harold, *The Measurement of Appearance*, 2nd ed, Wiley, N.Y., p. 410 (1987), call it translucency error. Spooner, Proc. of SPE-RETEC CAD, Charleston, S.C., Sept. 25–26, 1995, uses the term lateral diffusion error (LDE) to describe the process. All of these references are incorporated herein by reference.

Various methods have been developed to correct for this error. In "over-viewing" the area viewed by the detector is increased so that all of the light reflected by the sample, even the light which is laterally diffused out of the illuminated area, can be seen by the detector. ISO Ref. No. 5/4 1983 (E), International Organization for Standardization ("ISO 5/4"), incorporated herein by reference, which specifies geometry and optical parameters for measurement of reflectance density of photographic products, specifies that the boundary of the viewed area should be at least 2 mm beyond the edge of the illuminated area. In "over-illumination" the illuminated area is larger than the area viewed by the detector. If the conditions set forth in Clarke and Perry, "Helmholtz Reciprocity: its validity and application to reflectometry," Lighting Res. & Tech., 17 (1985), pp 1–11, are met, then the error reduction achieved will be the same whether the illumination or viewing area is increased by a similar amount. Spooner, SPE Color & Appearance Division RETEC Proc., Oct. 1–2, 1996, St. Louis, Mo., discloses a method for deriving a LDE correction which used measurements made at two positions relative to the instrument port.

When over-illumination, over-viewing, or two measurement position method is used to minimize LDE, it is assumed that the sample has a uniform surface and bulk content within all areas illuminated and viewed. The extent of over-illumination or over-viewing is highly dependent on the translucency of the sample. For instance, some translucent plastic samples require illumination/viewing aperture differences of 20 mm or more. According to ISO 5/4, only a 2 mm on the side difference is used to obtain a useful measurement of photo papers. An instrument designed for plastics measurements would minimize LDE when used for measuring photo papers. However, its aperture sizes might be impractical for the measurement of commonly used density wedges.

The methods for reducing LDE involve measuring the desired sample area and some area adjacent to the desired object area. In the printing industry, it is common practice to use color print control strips with 5 mm square elements. If the relative aperture size criteria of ISO 5/4 are used, then measuring a print control element could be accomplished by illuminating a 1 mm area in the center of the element and viewing a 5 mm area. However, if the element is printed using a halftone screen, this geometry may give a measured value that is dependent on the positioning of the object relative to the instrument. If the viewed area was increased to 5 mm and the illuminated area was increased to 9 mm, then illuminated areas of different color adjacent to the desired object area would affect the measurement. A reflectance measuring system that could illuminate the entire 5 mm square area and take measurements from the entire 5 mm area with little or no LDE uncertainty in the measured values would be highly desirable.

Thus, a need exists for a method that can give corrected reflectance values for translucent objects without the use of over-illumination-or over-viewing so that only a small area of the object is examined. Such a method should be able to provide corrected measurements for objects with a wide range of translucencies without requiring mechanical changes in aperture sizes.

SUMMARY OF THE INVENTION

The invention is a method that determines corrected reflectance values for translucent objects without the use of over-illumination or over-viewing and without requiring mechanical changes in aperture sizes once a calibration curve has been determined. This method derives a LDE corrected measurement value by viewing essentially only the area of the object lighted by the instrument illumination system.

The method comprises the steps of:
a) determining a uncorrected reflectance for a measured area of the object by:
   i) illuminating an area of the translucent object to produce the measured area,
   ii) measuring the spatial distribution of the light reflected by the measured area, and
   iii) calculating the uncorrected reflectance for the measured area;
b) calculating at least one SDV for the object:
c) determining a normalized LDE for the object by comparing the at least one SDV for the object with at least one predetermined relationship between SDV and normalized LDE, in which the number of SDVs for the object and the number of relationships is the same;
d) determining an LDE for the object from the normalized LDE;
e) calculating the corrected reflectance value for the object by adding the LDE for the object to the uncorrected reflectance.

In another embodiment, the invention is an apparatus for determining the corrected reflectance of an object.

BRIEF DESCRIPTION OF THE DRAWINGS

The invention can be more fully understood from the following description in connection with the accompanying drawings described as follows.

DETAILED DESCRIPTION OF THE INVENTION

Apparatus

Figure 1:
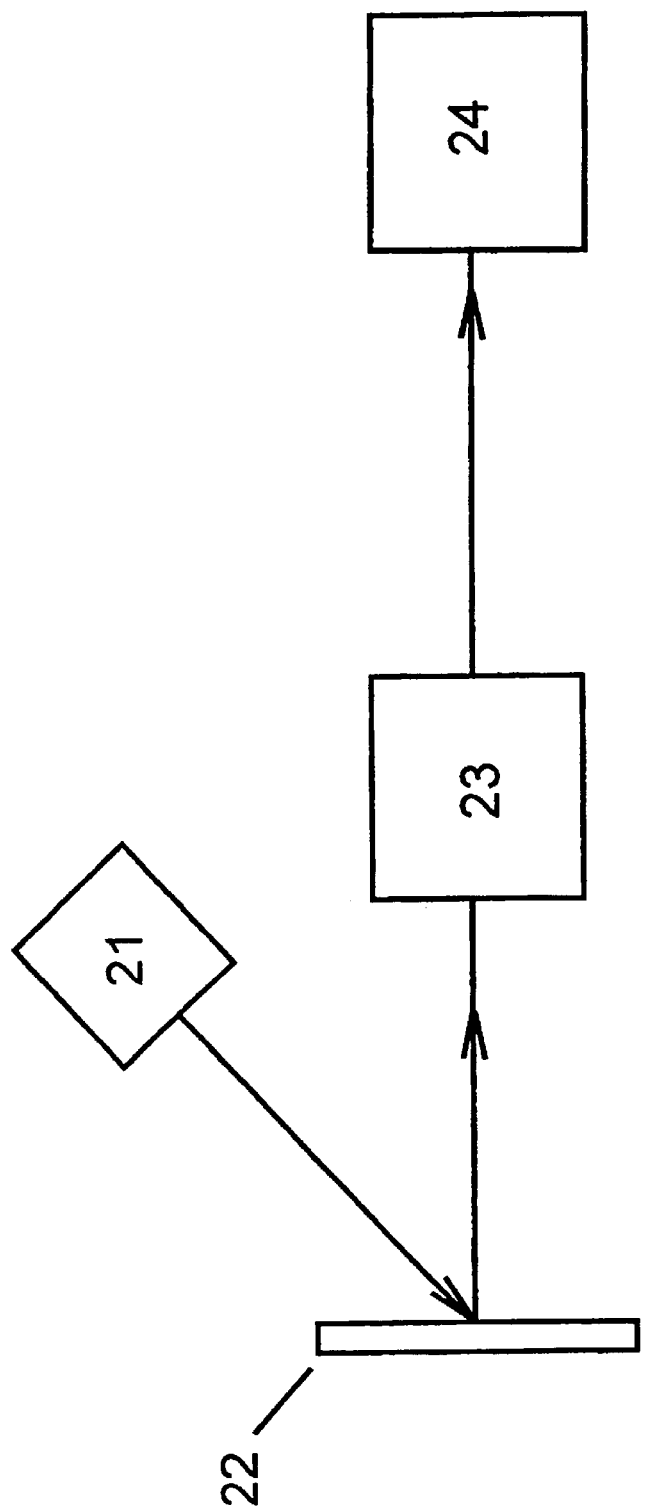
FIG. 1 shows an apparatus for carrying out the method of the invention.

FIG. 1 shows an apparatus for carrying out method of the invention. An area of translucent object 22 is illuminated by light source 21. Detector 23 measures the intensity distribution of the light reflected by the illuminated area of object 22. The signal is transmitted to computer 24. If necessary, the signal from the detector is digitized by an analog to digital (A/D) converter.

Computer 24 determines the total light received from the object by integrating the signal from the detector and also derives the spatial light distribution of the reflectance from the signal. The computer then determines the uncorrected reflectance by summing the components of the spatial pattern. It then computes a LDE correction value from a function of the light distribution and adds It to uncorrected reflectance value to determine the corrected reflectance value. The corrected reflectance value is then stored in a file or sent to an output device, such as a printer or display.

Light source 21 can be any natural or artificial light source known in the art, such as, for example, sunlight, an incandescent lamp, a fluorescent lamp, a mercury vapor lamp, a xenon lamp, a metal halide lamp, a laser, etc. Flash lamps may be used, such as a xenon flash lamp. The light source may also comprise other components well known in the art for controlling, directing, focusing, and/or transmitting light, such as, for example, shutters, output optics, apertures, mirrors, lenses, gratings, monochromators, filters, fiber optic bundles, integrating spheres, etc.

Detector 23 can be any detector known in the art for detecting radiation, such as a photomultiplier, a vacuum or solid state photodiode, a CCD array, a diode array detector, an assembly of spectral filtered photodiodes, etc. The detector may also comprise other components well known in the art for controlling, focusing, and/or transmitting light, such as, for example, shutters, output optics, apertures, mirrors, lenses, gratings, monochromators, filters, fiber optic bundles, etc.

In the method of the invention, light source 21 illuminates an area of translucent object 22. The physical size of the illuminated area is not important provided it is large enough to produce a representative reflectance value for the object. For example, in the measurement of halftone printed material, the area illuminated should be large enough to give a representative reflectance value independent of variation in sample position. In addition, the illuminated area should not be so large that the detector cannot measure a representative reflectance for the object.

Although collimated light or nearly collimated light may be used, it is not necessary. For example, the light source can be the port of an integrating sphere source. Typically, the light will be in the visible region of the spectrum, but the method is not limited to measurements in this region. The light may also be, for example, in ultraviolet or infrared regions of the spectrum. Typically polychromatic light is used, but monochromatic light from a laser or a monochromator can be used. As is apparent to those skilled in the art, if the reflectance at a single wavelength is desired, either the light source or the detector will comprise a monochromator or a filter, or a monochromatic light source, such as a laser, will be used. The light can be incident at 45° to the surface normal, but as apparent to those skilled in the art, other geometries can be used. When a reflector, such as a front surface mirror, is used as the object, the intensity of the light source can be measured. The measured intensity or intensities of the light source can be used to standardize the reflectance to account for differences in light sources using methods well known to those skilled in the art (see, for example, ASTM E 1164(83) and ISO Ref. No. 5/4 1983 (E)).

Then, the spatial pattern of the intensity of the light reflected by the illuminated area of the object is determined. If the illuminated area of the object is reasonably uniform, the intensity of the reflected light at the edges of the illuminated area will be lower than that reflected at the center of the illuminated area. The spatial pattern of the reflected light is determined with, for example, a black and white solid state camera chip, a segmented optical fiber assembly, etc. The spatial pattern of the reflected light is transferred to the computer.

The computer calculates the total light reflected (the uncorrected reflectance) by summing the components of the spatial pattern. The computer analyzes the spatial pattern and, as described below, derives a LDE value and adds it to the uncorrected reflectance to give the corrected reflectance value.

Figure 2:
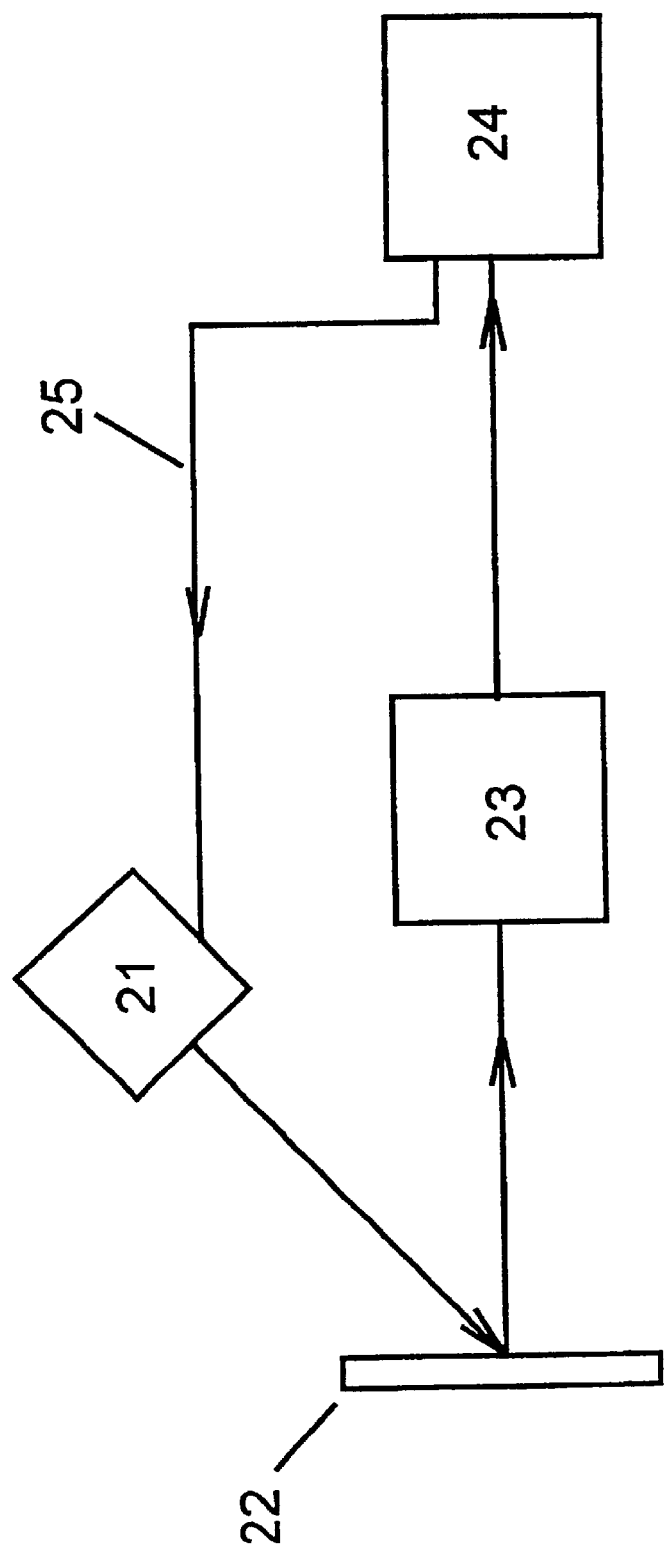
FIG. 2 shows an embodiment of an apparatus for carrying out the method of the invention.

FIG. 2 shows one embodiment of the apparatus. In this embodiment, light source 21 is a optical assembly (e.g. a fiber optic assembly) that sequentially illuminates two or more areas on the object. The object could also be illuminated by, for example, a CRT flying spot raster light source or a small spot source projected into a raster on the same using oscillating mirrors. The raster scan is started using the synchronizing signal from the computer. A single detector may be used to detect the reflected light.

Detector 23 is a wavelength scanning monochromator with detector or a grating with diode array, an assembly of spectral filtered photodiodes, or a single detector. In this embodiment, computer 24 generates synchronizing signal 25, which initiates the sequential illumination process.

Determination of the Relationship Between Normalized LDE and SDV

The relationship between normalized LDE and spatial distribution value (SDV) may be determined using a set of calibration standards. The standards should include samples that vary widely in translucency. Standards may include, for example, translucent plastics such as ABS, filled polymers, pigmented translucent plastics such as pigmented polymethylmethacrylate and other acrylate and methacrylate polymers and copolymers, polystyrene, paper, foods such as cheese, butter, etc.

Normalized linear diffusion error (LDE) is calculated by the following method. First a large area of each standard is illuminated and the spatial distribution of the reflectance of a portion of the illuminated area determined. The large illuminated area is called the illuminated area and the small measured area is called the measured area. The measured area should be far enough away from the edge of the illuminated area that the measurement is essentially free from lateral diffusion effects. Preferably, the measured area is at or near the center of the illuminated area.

Second, the illumination is adjusted so that only the measured area is illuminated. A second reflectance (S) is determined for the measured area. LDE is the difference in reflectance between first reflectance and the second reflectance. Normalized LDE is the LDE divided by the first reflectance:

$$\text{normalized } LDE = (L-S)/L$$

To determine SDV, the spatial pattern is divided into at least two concentric areas, preferably three concentric areas. Preferably the areas are of equal area.

The integrated reflectance of each of these regions is calculated. If two regions are used, a spatial distribution value (SDV) is calculated by subtracting the integrated reflectance of the outer region from the integrated reflectance of the inner region and dividing by the integrated reflectance of the inner region.

Figure 3:
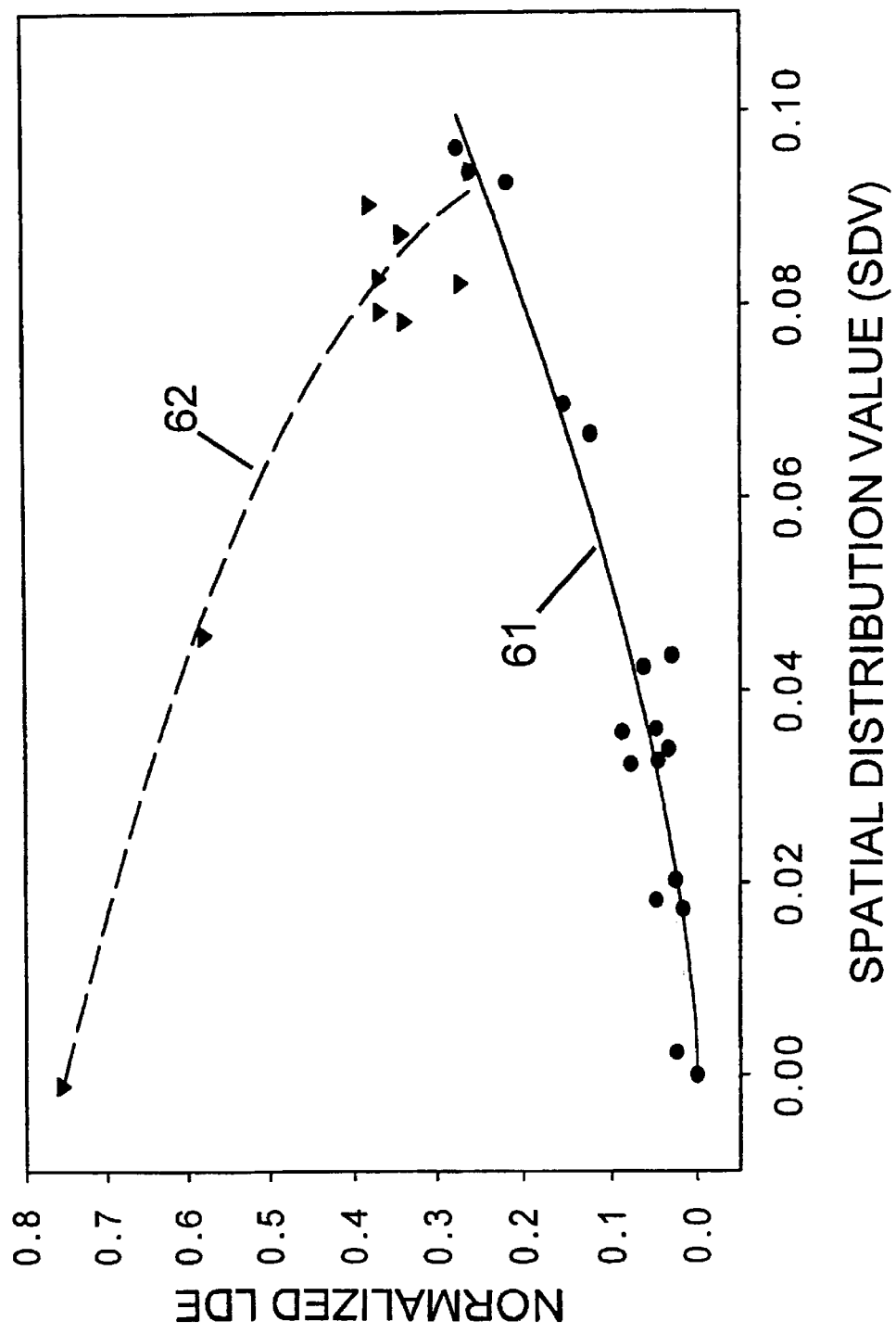
FIG. 3 is a plot of measurements and fitted functions of the normalized difference between the two channel detector system versus the normalized large area lateral diffusion error.

FIG. 3 shows a plot of normalized LDE versus spatial distribution value when two regions are used. To measure these values, a 45/0 narrow band (540 nm with 8 nm bandwidth) reflectometer using single beam illumination was set up on an optical bench. Twenty-nine samples of various translucencies were measured using both 38 and 8 mm diameter illumination and 8 mm viewing. Standards included pigmented polymers, filled polymers, paper, opal glass, pressed barium sulfate, etc.

The L values used for calculating the normalized LDEs shown in FIG. 3 were obtained with the 38 mm illumination and a 8 mm viewing aperture. The S values were obtained with 8 mm illumination and a 8 mm viewing apertures. A fiber bundle for viewing the center of the illuminated area surrounded by an adjoining coaxial ring of fibers which view the outer portion of the illuminated area was used to divided the reflectance into two equal areas. The spatial distribution value increases to a maximum and then decrease as the normalized LDE increases.

When three areas are used, two spatial distribution values are calculated. The first ($SDV_1$) is calculated by subtracting the integrated reflectance of the middle region from the integrated reflectance of the inner region and dividing by the integrated reflectance of the inner region. The second ($SDV_2$) is determined by subtracting the integrated reflectance of the outer region from the integrated reflectance of the inner region and dividing by the integrated reflectance of the inner region.

Figure 4:
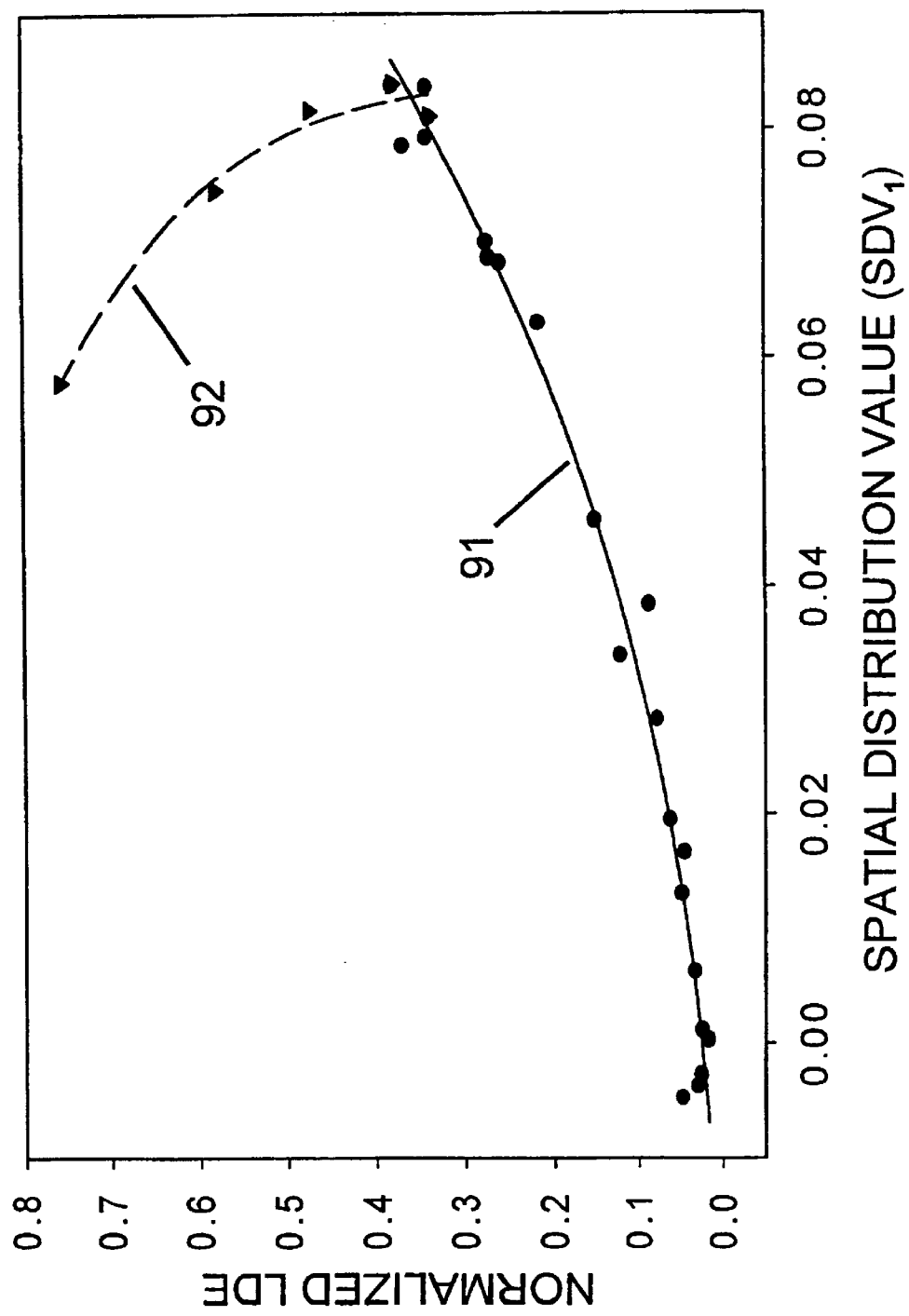
FIG. 4 is a plot of measurements and fitted functions of the normalized difference between the inner and middle areas of a three channel detector system versus the normalized lateral diffusion error.
Figure 5:
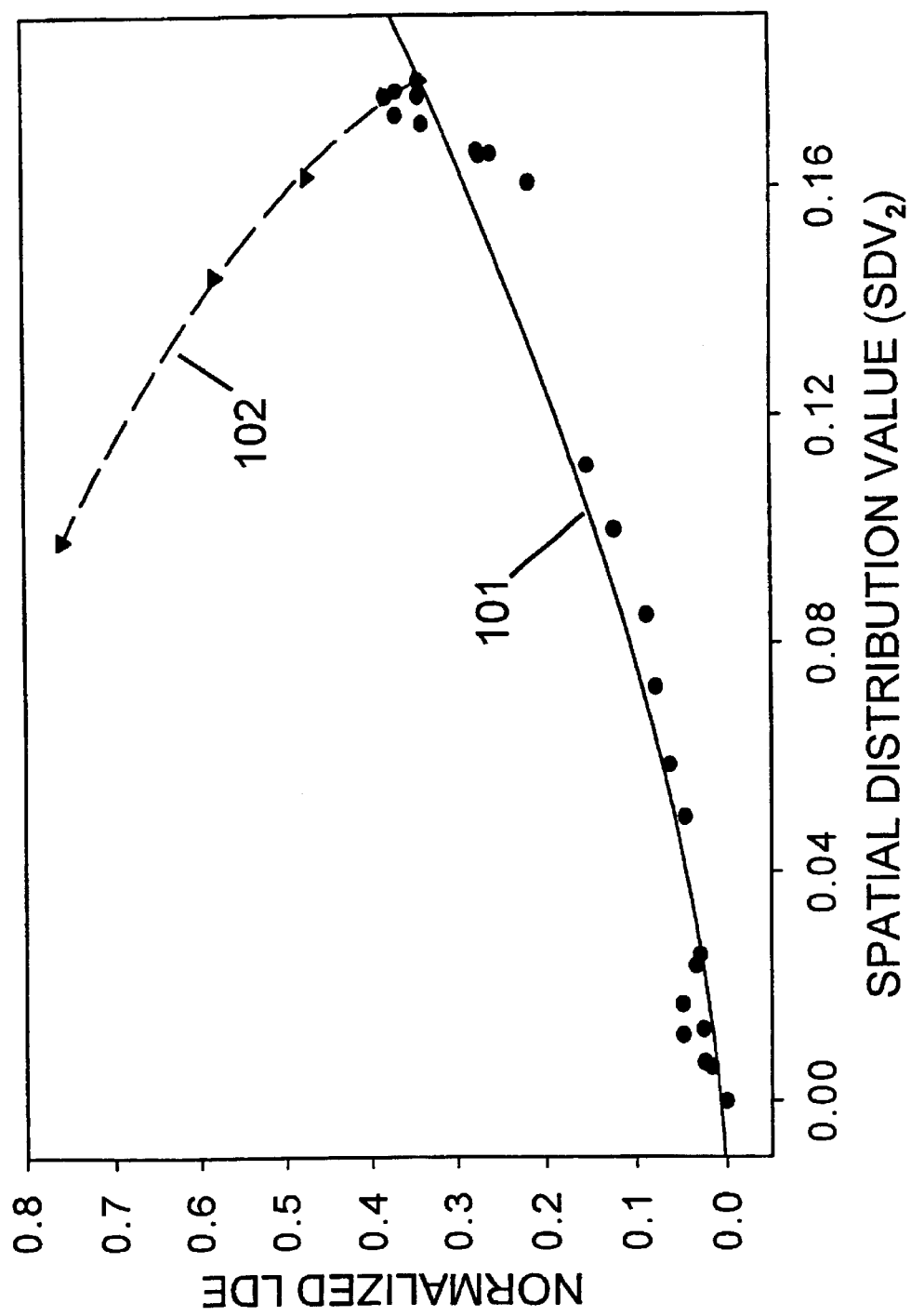
FIG. 5 is a plot of measurements and fitted functions of the normalized difference between the inner and outer elements of a three channel detector system versus the normalized lateral diffusion error.

FIG. 4 shows a plot of $SDV_1$ as a function of normalized LDE. FIG. 5 shows a plot of $SDV_2$ as a function of normalized LDE. This data were measured by a method similar to that used to measure the data in FIG. 3 except that a three channel fiber assembly consisting of a center bundle and two concentric ring bundles in which all three areas are approximately equal was used to divide the reflectance into three areas. Note that for certain SDVs the relationship between SDV and the normalized LDE is double-valued, i.e., a particular SDV is related to either of two normalized LDES.

Determination of Corrected Reflectance

The spatial pattern of reflectance is measured for the object and the spatial distribution value calculated as described above. For objects with medium to high opacity any of the calculated SDVs (SDV, $SDV_1$, or $SDV_2$) can be used to determine the normalized LDE using the relationship between SDV and normalized LDE. LDE is calculated from the normalized LDE and the sum the area reflectances used to generate the SDV [solving the equation:

$$\text{normalized } LDE = (L-S)/L$$

for (L−S), the LDE. The LDE is added to the uncorrected integrated reflectance of the object, i.e. the first reflectance, to give the corrected reflectance value for the object.

For other objects it is necessary to use $SDV_1$ and $SDV_2$ to determine the normalized LDE. As is apparent from FIGS. 4 and 5, for certain SDVs, the SDV is related to either of two normalized LDEs. However, the relationships shown in FIGS. 4 and 5 are not identical. To determine the normalized LDE, the two possible normalized LDEs are determined for each of $SDV_1$ and $SDV_2$ and compared. A single function that uses both relationships between SDV and normalized LDE may be used if desired. The normalized LDEs that most nearly coincide are used to determine the LDE. If the two values that most nearly coincide are not identical, the average of the two may used to determine the, normalized LDE. The normalized LDE is used to calculate the LDE and the corrected reflectance as described above.

In the determination of SDV, the image of the illuminated area may be conveniently divided into concentric equal areas by use of a fiber optic bundle. For two areas, it consists of a fiber bundle for viewing the center of the illuminated area surrounded by an adjoining coaxial ring of fibers which view the outer portion of the illuminated area. For the three area measurement, a three channel fiber assembly consisting of a center bundle and two concentric ring bundles is used in which all three areas are approximately equal.

Helmholtz's optical reciprocity, as defined by Clark and Perry, allows the light source and detector to be interchanged as long as certain conditions are met. Thus, a single channel detector can be used and the light source can be a moving spot scanner (e.g. a flying spot scanner or a two axis moving mirror system). Integrating a full raster scan gives the first, LDE containing, measurement value. A radial raster scan can be used to derive the reflectance intensity function used to derive the LDE.

INDUSTRIAL APPLICABILITY

The invention can be used to make accurate reflection measurements of translucent objects, such as paper, printed media, paint, plastics, textiles, and other manufactured product derived from animal sources, such as cheese, vegetable sources, or mineral sources. The invention can be used to make accurate reflection measurements in, for example, the paper, printing, coating, plastics, textile, and food industries by illuminating small areas of the object. The invention can also be used to make measurements used for formulation and for computer color matching of dyed and pigmented products.

Although the invention has been particularly shown and described with reference to certain preferred embodiments, those skilled in the art will appreciate that various modifications and changes in form and details may be made without departing from the spirit and scope of the invention. For example, although a single beam source was described, as is apparent to those skilled in the art, more than one illuminating beam could be used or an annular illuminating source could be used. Similarly, hemispherical illumination, as provided by an integrating sphere or other optical device, could also be used. Also, the detector can be, for example, a detector system consisting of a scanning monochromator with a single photodetector or a grating—diode array spectrometer system. Several detector systems, which can measure all of the fiber channels simultaneously, can be used. Helmholtz optical reciprocity would indicate the object could be illuminated serially in each of two or more region while a single detector views the object. The reflectance from the measured area can be divided into more than three areas if desired.

Having described the invention, we now claim the following and their equivalents.

What is claimed is:

1. A method for determining a corrected reflectance value for a translucent object, the method comprising the steps of:
    a) measuring a relationship between a normalized lateral diffusion error and a spatial distribution value for each of a set of calibration standards, by:
        i) illuminating an illuminated area of a standard and determining a first reflectance for a measured area of the standard,
        ii) illuminating only the measured area of the standard and determining a second reflectance for the measured area of the standard,
        iii) calculating the normalized lateral diffusion error for the standard from the first reflectance and the second reflectance,
        iv) determining the spatial distribution value for at least one of the first reflectance and the second reflectance,
        v) preparing a calibration curve showing the relationship between the normalized lateral diffusion error and the spatial distribution value for each standard;
    b) determining an uncorrected reflectance for a measured area of the object by:
        i) illuminating an area of the object to produce the measured area of the object,
        ii) measuring an uncorrected reflectance for the measured area of the object;
    c) determining at least one spatial distribution value for the measured area of the object from the reflectance of at least two concentric areas of the measured area of the object;
    d) determining a normalized lateral diffusion error for the uncorrected reflectance of the measured area of the object from the spatial distribution value for the measured area of the object and the calibration curve; and
    e) calculating the corrected reflectance value from the uncorrected reflectance for the measured area of the object and the normalized lateral diffusion error;
    in which:
        the illuminated area of the standard is larger than the measured area of the standard; and
        the measured area of the standard is far enough away from the edge of the illuminated area of the standard to be essentially free from diffusion effects.

2. The method of claim 1 one spatial distribution value is determined for the measured area of the object.

3. The method of claim 2 in which the object is illuminated by visible radiation.

4. The method of claim 3 in which the corrected reflectance value is determined at a single wavelength.

5. The method of claim 4 in which the object Is illuminated by a scanning light source.

6. The method of claim 5 in which the scanning light source is produced by serially illuminating the segments of a coaxially segmented fiber optical system.

7. The method of claim 1 in which the object is illuminated by visible radiation.

8. The method of claim 1 in which the corrected reflectance value is determined at a single wavelength.

9. The method of claim 1 In which the object is illuminated by a scanning light source.

10. The method of claim 9 in which the scanning light source is produced by serially illuminating the segments of a coaxially segmented fiber optical system.

11. The method of claim 1 in which the measured area of the standard is at or near the center of the illuminated area of the standard.

12. A method for determining a corrected reflectance value for a translucent object, the method comprising the steps of:
    a) measuring a relationship between a normalized lateral diffusion error and a spatial distribution value for each of a set of calibration standards, by:
        i) illuminating an illuminated area of a standard and determining a first reflectance for a measured area of the standard,
        ii) illuminating only the measured area of the standard and determining a second reflectance for the measured area of the standard,
        iii) calculating the normalized lateral diffusion error for the standard from the first reflectance and the second reflectance,
        iv) determining the spatial distribution value for at least one of the first reflectance and the second reflectance,
        v) preparing a calibration curve showing the relationship between the normalized lateral diffusion error and the spatial distribution value for each standard;
    b) determining an uncorrected reflectance for a measured area of the object by:
        i) illuminating an area of the object to produce the measured area of the object, ii) measuring an uncorrected reflectance for the measured area of the object;

c) determining at least one spatial distribution value for the measured area of the object from the reflectance of at least two concentric areas of the measured area of the object;

d) determining a normalized lateral diffusion error for the uncorrected reflectance of the measured area of the object from the spatial distribution value for the measured area of the object and the calibration curve; and e) calculating the corrected reflectance value from the uncorrected reflectance for the measured area of the object and the normalized lateral diffusion error;

in which:
the illuminated area of the standard is larger than the measured area of the standard;
the measured area of the standard is far enough away from the edge of the illuminated area of the standard to be essentially free from diffusion effects; and
two spatial distribution values are determined for the measured area of the object.

13. The method of claim 12 in which the object is illuminated by visible radiation.

14. The method of claim 13 in which the corrected reflectance value is determined at a single wavelength.

15. The method of claim 14 in which the object is illuminated by a scanning light source.

16. The method of claim 15 in which the scanning light source is produced by serially illuminating the segments of a coaxially segmented fiber optical system.

17. An apparatus for determining a corrected reflectance value for a translucent object, the apparatus comprising:

a light source that sequentially illuminates all regions of the object within a sampled area;

a detector that measures the intensity of the light reflected by the sequentially illuminated regions of the sampled area of the object;

a computer that:
generates a synchronizing signal that initiates the sequential illumination,
calculates an uncorrected reflectance by summing the components of a spatial light pattern produced by the sequential illumination,
derives a normalized lateral diffusion error, and
adds the normalized lateral diffusion error and the uncorrected reflectance to give the corrected reflectance;
in which the light source that sequentially illuminates all regions of the object within the sampled area comprises a coaxially segmented fiber optical system.

18. The apparatus of claim 17 in which:
the apparatus additionally comprises an output device and,
the computer sends the corrected reflectance to the output device.

19. The apparatus of claim 17 in which the coaxially segmented fiber optical system is a three channel fiber assembly consisting of a center bindle and two concentric ring bundles.

20. The apparatus of claim 17 in which the coaxially segmented fiber optical system is a fiber bundle surrounded by an adjoining coaxial ring of fibers.

* * * * *